US010034644B2

(12) United States Patent
Mizuta

(10) Patent No.: US 10,034,644 B2
(45) Date of Patent: Jul. 31, 2018

(54) TOMOGRAPHIC IMAGE DISPLAY DEVICE

(71) Applicant: Shimadzu Corporation, Kyoto (JP)

(72) Inventor: Tetsuro Mizuta, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 0 days.

(21) Appl. No.: 15/528,075

(22) PCT Filed: Sep. 4, 2015

(86) PCT No.: PCT/JP2015/075261
§ 371 (c)(1),
(2) Date: May 18, 2017

(87) PCT Pub. No.: WO2016/080054
PCT Pub. Date: May 26, 2016

(65) Prior Publication Data
US 2017/0319163 A1    Nov. 9, 2017

(30) Foreign Application Priority Data

Nov. 18, 2014  (JP) .................................. 2014-233661

(51) Int. Cl.
*A61B 6/00* (2006.01)
*A61B 6/03* (2006.01)
*G06T 11/00* (2006.01)

(52) U.S. Cl.
CPC .............. *A61B 6/469* (2013.01); *A61B 6/032* (2013.01); *A61B 6/466* (2013.01); *G06T 11/003* (2013.01)

(58) Field of Classification Search
CPC ......... A61B 6/469; A61B 6/466; A61B 6/032; G06T 11/003

(Continued)

(56) References Cited

U.S. PATENT DOCUMENTS

2014/0294138 A1* 10/2014 Jerebko .................. A61B 6/025
378/4

FOREIGN PATENT DOCUMENTS

JP    2007-163154 A    6/2007

OTHER PUBLICATIONS

Kazuhiro Katahira, "Comfort 3D Imaging Method and System Design for Feasibility—Usefulness of Evolving Sliding Thin Slab MIP Method" Innervision (24-3), 2009, p. 118-119.

* cited by examiner

*Primary Examiner* — Amandeep Saini
(74) *Attorney, Agent, or Firm* — Muir Patent Law, PLLC

(57) ABSTRACT

In a tomographic image display device, an MIP-axis setting unit sets a predetermined axis of a subject as an MIP-axis. A position information calculation unit sets each position of three-dimensional volume data obtained for different regions of interest at three-dimensional positions corresponding to positional relationships between the MIP-axis and the region of interest. A three-dimensional data integration unit integrates each of the three-dimensional volume data in which three-dimensional positions are set into single three-dimensional data, and an MIP image generation unit projects an MIP image onto the integrated three-dimensional data in one or more projection directions orthogonal to the MIP-axis. In the MIP image, projection images of each of three-dimensional volume data are projected at positions corresponding to a positional relationship between the MIP-axis and the regions of interest. Consequently, by referring to a single MIP image, diagnoses can be performed by associating a plurality of regions of interest with a position of a predetermined axis of a subject.

5 Claims, 13 Drawing Sheets

(58) Field of Classification Search
USPC .......................................................... 382/131
See application file for complete search history.

TOMOGRAPHIC IMAGE DISPLAY DEVICE

TECHNICAL FIELD

The present invention relates to a technology for generating an image suitable for doctor's diagnoses and performing image processing for displaying the image based on image data showing a three-dimensional distribution of radiopharmaceuticals administered to a subject.

TECHNICAL BACKGROUND

In a medical filed, nuclear medical diagnosis equipment is used, in which radiations (example, γ rays) emitted from radiopharmaceuticals administered to a subject and localized at regions of interest are detected and a tomographic image of a radiopharmaceutical distribution in the regions of interest of the subject is obtained. As popular nuclear medical diagnosis equipment, a PET (Positron Emission Tomography) device, a SPECT (Single Photon Emission Computed Tomography) device, etc., are known. In such nuclear medical diagnosis equipment, three-dimensional volume data showing a concentration distribution of radioactive pharmaceuticals is reconfigured using radiation detection data. Then, the equipment displays a tomographic image at a predetermined slice cross-section based on the three-dimensional volume data, so that a diagnosis is performed.

As a display method for overviewing an entire tomographic image obtained by conventional nuclear medical diagnosis equipment, a maximum intensity projection method (MIP: Maximum Intensity Projection) is widely used. A maximum intensity projection image (MIP image) projected by the MIP is an image in which the maximum pixel value in the projection path is set as a luminance value at the time of projecting an object. A plurality of MIP images projected in a plurality of directions in which a predetermined direction is set as a central axis are generated, and using a tomographic image display device, these plural MIP images are displayed like, for example, a rotating moving image (see, e.g., Patent Document 1). Hereinafter, the predetermined direction which becomes a central axis at the time of generating a series of MIP images is denoted as "MIP-axis".

When generating a series of MIP images, as shown in FIG. 14A, with respect to three-dimensional volume data of a region of interest R, for example, an MIP image A1 is acquired in a projection direction S1 parallel to the x-direction, and an MIP image A2 is acquired in a projection direction S2 parallel to the y-direction. By referring to the MIP image A1 and the MIP image A2 acquired in different projection directions, an operator can intuitively know the approximate position P of the region in which radioactive pharmaceuticals are integrated in the region of interest R.

As described above, the image display method by the MIP is very useful for confirming the approximate information before scrutiny diagnosing the tomographic image. In FIG. 14A, MIP images are generated in a manner such that the axis S3 which passes through the center point of the region of interest R and is parallel to the z-axis is set as an MIP-axis.

In nuclear medicine diagnoses, as shown in FIG. 14B, in cases where a region of interest is a whole-body of a subject M or within a range R1 on the median line, a series of MIP images are generated in a manner such that the median line L1 of the subject M is set as an MIP-axis. On the other hand, in cases where a region of interest is a shoulder portion shown by the symbol R2 or the like, there is a case in which the median line L1 falls outside the range of the region of interest.

Under the circumstance, conventionally, a method (Sliding Thin Slab MIP method; hereinafter abbreviated as "Sliding method") is used, in which a series of MIP images are generated while moving the MIP-axis toward the center line of a region of interest in accordance with the movement of the region of interest (see, e.g., Non-Patent Document 1). In the sliding method, when the region of interest is within a range R2, the projection of the MIP image is performed by moving the MIP-axis from the median line L1 to the center line L2 of the range R2. By such a method, with respect to a local region away from the median line, a series of MIP images with less blur of each projection position can be acquired.

PRIOR ART DOCUMENT

Patent Document

Patent Document 1: Japanese Unexamined Patent Application Publication No. 2007-163154

Non-Patent Document

Non-Patent Document 1: Kazuhiro KATAHIRA, "Comfort 3D Imaging Method and System Design for Feasibility—Usefulness of Evolving Sliding Thin Slab MIP Method" INNERVISION (24-3), 2009, p. 118-119

SUMMARY OF THE INVENTION

A conventional tomographic image display device using such a sliding method is useful in cases where only a specific region distant from the median line is locally diagnosed like in a case of tracking a vascular area. However, in a state in which whole-body image information of a subject is being acquired, when an MIP image is further acquired to obtain high resolution image information on a specific region, it is difficult for a conventional device to obtain useful information. That is, it is very difficult to know the detail information in which the high resolution MIP image obtained for the specific region is added to the whole image of the subject.

Conventional problems will be concretely explained with reference to FIG. 14B. For example, in cases where MIP images for the region R2 as a specific region are acquired, the MIP-axis becomes L2 passing through the center point of the region R2. On the other hand, the MIP-axis for the whole-body of the subject M is a median line L1 of the subject M. Thus, the whole-body image of the subject and the MIP image of the specific region are different in MIP-axis. In cases where the MIP-axis is different, the MIP images obtained for the whole-body and the MIP images obtained for the specific region are mismatched in the relative positional relationship. Therefore, even if the MIP images for the specific region R2 and the MIP images for the whole-body are compared and considered, it is not possible to obtain the information that the radiopharmaceutical image appeared in the MIP image corresponds to which region of the whole-body of the subject.

Further, in the case of acquiring a series of MIP images for two or more separated specific regions, each of MIP images is different in the MIP-axis position. Therefore, the positional information of radiopharmaceuticals obtained for each specific region cannot be diagnosed comprehensively. For example, when MIP images for the breast of the left chest as a specific region and MIP images for the breast of the right chest as a specific region are acquired, the MIP images of the left chest are images in which the left chest is arranged at the center of each of images. On the other hand, the MIP images of the right chest are images in which the right chest is arranged at the center of each of images.

It is possible to separately diagnose the MIP images of the left chest and the MIP images of the right chest. However, the MIP images of the left chest and the MIP images of the right chest are different in the region reflected at the center of the image, and therefore each breast cannot be diagnosed comprehensively using each group of MIP images. Further, since the image reflected at the center of the MIP image is located at the center of the specific region, it is difficult to diagnose in an overall manner by associating the position information of radiopharmaceuticals obtained for each of the left chest and the right chest with the whole-body or the whole chest.

The present invention was made in view of the aforementioned circumstances, and aims to provide a tomographic image display device capable of generating and displaying an image suitable for diagnosing more diverse regions of interest.

Means for Solving the Problems

Embodiments described herein have the following configuration that may attain the aforementioned objects. A tomographic image display device according to certain embodiments of the present invention may include three-dimensional data generation means for generating three-dimensional volume data showing a generation position of radiation in a region of interest of a subject based on the radiation generated from the region of interest of the subject, central axis setting means for setting a predetermined axis in the subject as a central axis, alignment means for setting a three-dimensional position of the three-dimensional volume data to a three-dimensional position of the region of interest with respect to the central axis, MIP image generation means for generating an MIP image which is a maximum intensity projection image by projecting a maximum pixel value in one or more projection directions orthogonal to the central axis with respect to the three-dimensional volume data in which the three-dimensional position is set by the alignment means, tomographic image generation means for generating a tomographic image at a predetermined slice surface of the three-dimensional volume data, and image display means for displaying the MIP image and the tomographic image.

The tomographic image display may include central axis setting means for setting a predetermined axis in the subject as a central axis, and alignment means for setting a three-dimensional position of the three-dimensional volume data to a three-dimensional position of the region of interest with respect to the central axis. In this case, the positional relationship between the position of the three-dimensional volume data set by the alignment means and the central axis coincide with the positional relationship between the region of interest and the central axis.

The MIP image generation means may generate an MIP image which is a maximum intensity projection image by projecting a maximum pixel value in one or more projection directions orthogonal to the central axis with respect to the three-dimensional volume data in which the three-dimensional position is set by the alignment means. Since all of the projection directions of the MIP images are orthogonal to the central axis, the central axis is an axis passing through the center point of the MIP image. Further, in each of the MIP images, a projection image of the three-dimensional volume data is reflected at a position corresponding to the position of the region of interest with respect to the central axis. Therefore, an operator can observe each of the MIP images acquired for the region of interest in an overview manner and easily analyze the positional relationship between the radiation generation position in the region of interest and the predetermined axis of the subject. Accordingly, in the device according to the present invention, it is possible to perform more various diagnosis using MIP images.

Further, in the aforementioned invention, it is preferable that the device further include three-dimensional data integration means for integrating a plurality of the three-dimensional volume data in which the three-dimensional position is set by the alignment means and converting them into single integrated three-dimensional volume data, and that the MIP image generation means generate the MIP image in one or more projection directions orthogonal to the central axis with respect to the integrated three-dimensional volume data converted by the three-dimensional data integration means.

According to some examples of the tomographic image display device of the present invention, a three-dimensional data integration means is provided for integrating a plurality of three-dimensional volume data in which the three-dimensional position is set by the alignment means and converting them into single three-dimensional volume data. The MIP image generation means generates the MIP image in one or more projection directions orthogonal to the central axis with respect to the integrated three-dimensional volume data converted by the three-dimensional data integration means.

Each of the three-dimensional volume data is converted into single integrated three-dimensional volume data, and an MIP image is generated based on the integrated three-dimensional volume data. Since all of the projection directions of the MIP images are orthogonal to the central axis, in each of the MIP images, the central axis is an axis passing through the center point of the MIP image. In each of the MIP images, the projection image of the three-dimensional volume data related to each region of interest is reflected at the position of each region of interest with respect to the central axis. That is, projection images of a plurality of regions of interest appear at positions of a single MIP image with respect to the central axis, respectively.

In this case, an overview diagnosis can be performed on a plurality of regions of interest based on the single MIP image. Therefore, by using the MIP image, it is possible to reduce the burden on the operator when a plurality of regions are diagnosed. Also, the MIP images are generated for a pre-integrated single three-dimensional volume data. Therefore, even in cases where the number of regions of interest to be diagnosed is large, it is possible to avoid complication of calculation required for generating MIP images. Therefore, it is possible to suitably avoid the degradation of the diagnosis workflow.

Further, in some examples, it may be preferable that the device include MIP image integration means for generating an integrated MIP image by superimposing the MIP images projected in the same projection direction among the MIP images generated for a plurality of regions of interest with reference to a position of the central axis, and that the image display means display the integrated MIP image.

According to some examples of the tomographic image display device of the present invention, the MIP image integration means superimposes MIP images projected in the same projection direction among the MIP images generated for a plurality of regions of interest respectively with reference to the position of the central axis to generate an integrated MIP image. In each of the MIP images, the central axis is an axis passing through the center point of the image, and the projection images of the three-dimensional volume data related to the regions of interest are displayed at the position of each region of interest with respect to the central axis, respectively. Therefore, by superimposing each of MIP images with reference to the central axis, the maximum value projection images for a plurality of regions of interest appear in the integrated MIP image at positions with reference to the central axis.

In this case, an overview diagnosis can be performed on a plurality of regions of interest based on a single MIP image. Therefore, it is possible to reduce the burden on the operator when a plurality of regions are diagnosed using the MIP image. In addition, the integrated MIP image is generated not by integrating three-dimensional volume data but by integrating MIP images, which are two-dimensional images. Therefore, calculation for generating MIP images in which a plurality of regions of interest appear at positions with reference to the central axis becomes simpler, so that the time required for diagnosis can be further shortened. Therefore, it is possible to further improve the diagnosis workflow.

Further, in some examples, it may be preferable that the device further include superimposed image generation means for generating a superimposed image by superimposing an image in which all or a part of the subject is projected in the same projection direction as the MIP image on each of the MIP images generated by the MIP image generation means with reference to the position of the central axis and that the image display means display the superimposed image.

According to some examples, the superimposed image generation means may generate a superimposed image by superimposing an image obtained by projecting all or a part of the subject in the same projection direction as the MIP image on each of the MIP images with reference to the position of the central axis. By performing superimposing with reference to the position of the central axis, the positional relationship between the image in which all or a part of the subject is projected and the region of interest of the MIP image coincide with the positional relationship between both of them in the body of the subject.

Therefore, by referring to the image of the subject to be superimposed on the MIP image, a projection image of the three-dimensional volume data is reflected at a position corresponding to the position of the region of interest with respect to the central axis. Therefore, the operator can observe each of the superimposed images acquired for the region of interest in an overview manner and more accurately and easily analyze the positional relationship between the radiation generation position in the region of interest and the body of the subject. Accordingly, in the device according to the present invention, it is possible to perform more various diagnoses using MIP images.

Further, in some examples, it may be preferable that the central axis be a median line of the subject.

According to some examples of the tomographic image display device of the present invention, the central axis setting means sets the median line of the subject as a center line. In this case, in each of the MIP images, the median line is an axis passing through the center of the image, and the projection image of the three-dimensional volume data for the region of interest is reflected at the position of regions of interest with respect to the median line. Therefore, the operator can diagnose the information obtained from the projection image of the region of interest in association with an image more suitable for analysis exemplified by a whole body of a subject, etc.

The tomographic image display device may include central axis setting means for setting a predetermined axis in the subject as a central axis, and alignment means for setting a three-dimensional position of the three-dimensional volume data to a three-dimensional position of the region of interest with respect to the central axis. In this case, the positional relationship between the position of the three-dimensional volume data set by the alignment means and the central axis coincide with the positional relationship between the region of interest and the central axis.

The MIP image generation means may generate an MIP image which is a maximum intensity projection image by projecting a maximum pixel value in one or more projection directions orthogonal to the central axis with respect to the three-dimensional volume data in which the three-dimensional position is set by the alignment means. Since the projection direction of the MIP image is orthogonal to the central axis, the central axis is an axis passing through the center point of the MIP image. Further, in each of the MIP images, a projection image of three-dimensional volume data is displayed at a position corresponding to the position of the region of interest with respect to the central axis. Therefore, the operator can observe each of the MIP images acquired for the region of interest in an overview manner and easily analyze the positional relationship between the radiation generation position in the region of interest and the predetermined axis of the subject. Accordingly, it is possible to perform more various diagnoses using MIP images.

BRIEF DESCRIPTION OF THE DRAWINGS

FIG. 1 is a schematic view explaining a configuration of a PET device equipped with a tomographic image display device according to Embodiment 1.

FIG. 3 is a flowchart explaining operation steps of the PET device equipped with the tomographic image display device according to each Embodiment.

FIG. 7 is a view explaining projection directions of MIP images in Step S6 according to Embodiment 1.

FIG. 10 is a view explaining a process of Step S8 according to Embodiment 1.

FIG. 11 illustrates a comparison between a conventional Embodiment and an Embodiment.

FIG. 14 is a view showing problems in a conventional embodiment.

EMBODIMENTS FOR CARRYING OUT THE INVENTION

Embodiment 1

Figures 1A, 1B:
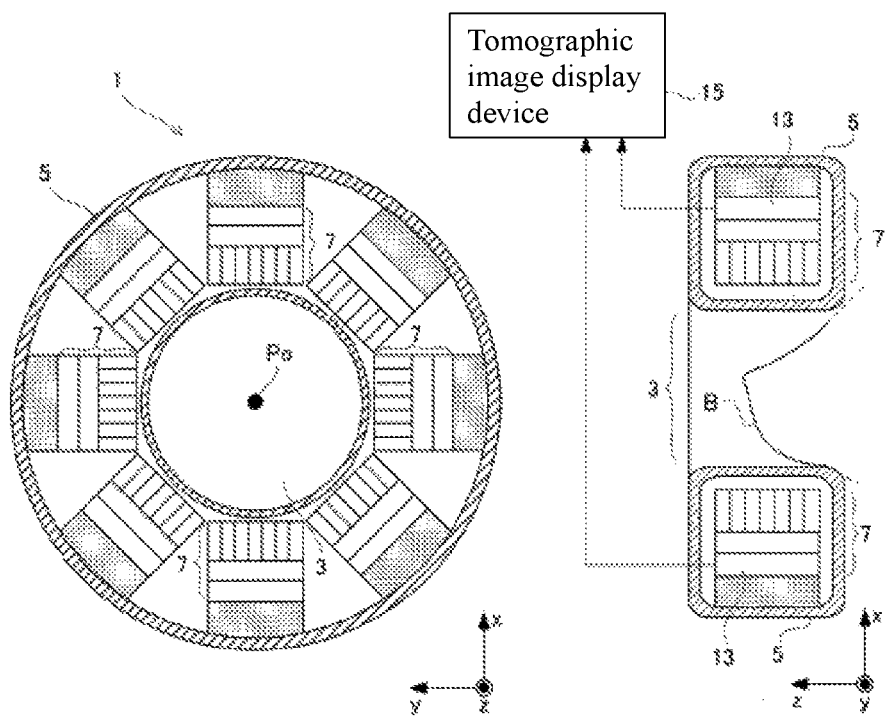
FIG. 1A is a vertical cross-sectional view in an x-y plane.
FIG. 1B is a vertical cross-sectional view in an x-z plane.

Hereinafter, Embodiment 1 of this invention will be described with reference to drawings. FIG. 1A is a vertical cross-sectional view in an x-y plane of nuclear medical diagnosis equipment equipped with a tomographic image display device according to Embodiment 1. FIG. 1B is a vertical cross-sectional view in an x-z plane of the nuclear medical diagnosis equipment equipped with the tomographic image display device according to Embodiment 1. In Embodiment 1, as the nuclear medical diagnosis equipment, the following explanation will be made by exemplifying a breast dedicated PET device used for breast cancer diagnoses. Further, the explanation will be made using a γ ray as an example of radiation.

<Description of Overall Configuration>

A PET device 1 equipped with a tomographic image display device according to Embodiment 1 will be described. As shown in FIG. 1A and FIG. 1B, the PET device 1 is equipped with a gantry 5 having an introduction hole 3 for introducing a breast B of a subject. In the gantry 5, a plurality of radiation detectors 7 arranged in a ring shape so as to surround the introduction hole 3. The introduction hole 3 has a cylindrical configuration extending in the z-direction (introduction direction of the breast B). The x-direction is a body axis direction of a subject taking a standing posture or a sitting posture. The y-direction is a direction orthogonal to the x-direction and the z-direction and corresponds to the horizontal direction of the subject.

Figure 1C:
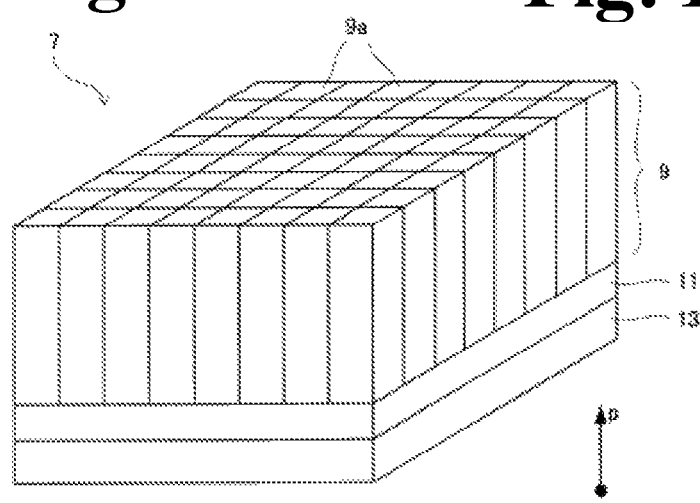
FIG. 1C is an overhead view explaining a laminate structure of a radiation detector.

The radiation detector 7 has, as shown in FIG. 1C, a configuration in which a scintillator block 9, a light guide 11, and a light detector 13 are stacked in order in a p-direction. The p-direction is a direction toward the center Po of the introduction hole 3, and each of radiation detectors 7 is arranged so that the scintillator block 9 is arranged closer to the center Po than the light detector 13.

The scintillator block 9 has a configuration in which rectangular parallelepiped scintillator crystals 9a are arranged two dimensionally, and is configured to absorb γ rays emitted from a subject and emit scintillator light. As the material configuring the scintillator crystals 9a, crystals, such as, e.g., LYSO, LSO, or LGSO, are used.

The light guide 11 transmits scintillator light emitted by the scintillator block 9 to the light detector 13. The light detector 13 is provided with photoelectric conversion elements, and is configured to detect scintillator light and convert the scintillator light to an electric signal (γ ray detection signal). The tomographic image display device 15 performs various processing based on the γ ray detection signal output from the light detector 13, and generates and displays various images showing a distribution of radiopharmaceuticals in the breast B.

Figure 2:
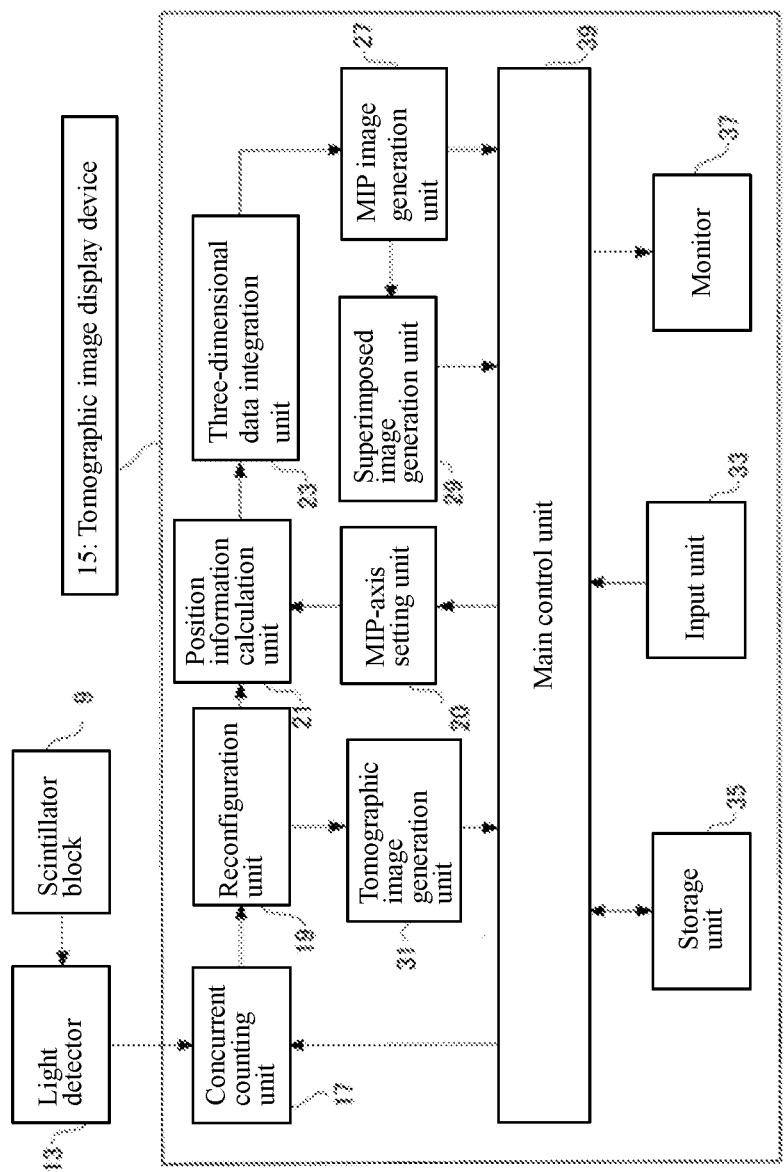
FIG. 2 is a functional block diagram explaining a configuration of a PET device equipped with the tomographic image display device according to Embodiment 1.

The tomographic image display device 15 is equipped with, as shown in FIG. 2, a concurrent counting unit 17, a reconfiguration unit 19, an MIP-axis setting unit 20, a position information calculation unit 21, a three-dimensional data integration unit 23, an MIP image generation unit 27, a superimposed image generation unit 29, and a tomographic image generation unit 31. The concurrent counting unit 17 is provided at the post-stage of the light detector 13, and judges whether the γ ray detection signal output from the light detector 13 is proper data.

When radiopharmaceuticals are administered to a subject M, the radioactive pharmaceuticals are accumulated in the regions of interest, and positrons are emitted from the accumulated drug. The emitted positrons cause annihilation with electrons, and emit a pair of annihilation γ ray pair having exactly opposite momentum. The concurrent counting unit 17 judges that a pair of γ rays concurrently incident to a pair of scintillator blocks 9 facing each other across the center point Po is the annihilation γ ray pair caused by radiopharmaceuticals in a subject. Then, the concurrent counting unit 17 judges that the γ ray direction signal based on the annihilation γ ray pair is proper data, and transmits the γ ray detection signal judged as proper data to the reconfiguration unit 19. The concurrent counting unit 17 judges that γ rays incident to only one of the pair of scintillator blocks 9 is a noise and rejects the γ ray detection signal based on the γ ray judged as a noise.

The reconfiguration unit 19 reconfigures the γ ray detection signal output from the concurrent counting unit 17 as proper data to generate three-dimensional volume data. The three-dimensional volume data is data showing a three-dimensional distribution of radiopharmaceuticals administered to a subject, and shows a generation position of radiation in the region of interest of the subject. The MIP-axis setting unit 20 sets a predetermined axis of a subject specified by an operator as an MIP-axis. The MIP-axis denotes an axis orthogonal to each of directions for projecting an MIP image with respect to three-dimensional volume data. The reconfiguration unit 19 corresponds to three-dimensional data generation means of the present invention. The MIP-axis setting unit 20 corresponds to central axis setting means of the present invention. The MIP-axis corresponds to a central axis of the present invention.

The position information calculation unit 21 is arranged at the post-stage of each of the reconfiguration unit 19 and the MIP-axis setting unit 20, and calculates the positional information of regions of interest based on a predetermined position on the MIP-axis for each of three-dimensional volume data. Further, the position information calculation unit 21 performs alignment of each of three-dimensional volume data obtained from regions of interest different from each other based on the calculated positional information. The position information calculation unit 21 corresponds to alignment means of the present invention.

The three-dimensional data integration unit 23 is provided at the post-stage of the position information calculation unit 21, and integrates each of aligned three-dimensional volume data as single three-dimensional volume data that cover all of three-dimensional volume. The MIP image generation unit 27 is provided at the post-stage of the three-dimensional data integration unit 23, and generates an MIP image which is a maximum intensity projection image based on the three-dimensional volume data integrated by the three-dimensional data integration unit 23. The three-dimensional data integration unit 23 corresponds to the three-dimensional data integration means of the present invention. The image generation unit 27 corresponds to the MIP image generation means of the present invention.

The superimposed image generation unit 29 is provided at the post-stage of the MIP image generation unit 27. The superimposed image generation unit 29 generates a series of superimposed images by superimposing an image (for example, a whole-body image of a subject) serving as a reference for comparison on each of the series of MIP images with reference to the position of the MIP axis. The tomographic image generation unit 31 generates a tomographic image in a slice surface specified by an operator based on the three-dimensional volume data generated by the reconfiguration unit 19. The superimposed image generation unit 29 corresponds to the superimposed image generation means of the present invention, and the tomographic image generation unit 31 corresponds to the tomographic image generation means of the present invention.

The tomographic image display device 15 is further provided with an input unit 33, a storage unit 35, a monitor 37, and a main control unit 39. The input unit 33 is configured to input an instruction of an operator, and is exemplified by, for example, a keyboard input type panel and a touch input type panel. The storage unit 35 stores information on three-dimensional volume data, tomographic images, etc. Further, the storage unit 35 preliminary stores an image to be superimposed on each of MIP images and an image serving as an alignment reference for three-dimensional volume data. Examples of an image to be superimposed on an MIP image and an image serving as an alignment reference include, for example, a whole-body image of a subject and an entire image of a chest portion.

The monitor 37 displays various images, such as, e.g., three-dimensional volume data, a tomographic image, and a superimposed image. The main control unit 39 is configured by, for example, a central processing unit (CPU), and comprehensively controls each configuration of the concurrent counting unit 17, etc., provided in the tomographic image display device 15. The monitor 37 corresponds to the image display means of the present invention.

<Description of Operation>

Next, the operation of the PET device 1 equipped with a tomographic image display device according to Embodiment 1 will be described. FIG. 3 is a flowchart explaining operation steps of the PET device equipped with the tomographic image display device according to Embodiment 1. In Embodiment 1, it is assumed that each of right and left breasts is set as a region of interest and each image data thereof is acquired.

Step S1 (Setting of MIP-axis)

In operating the PET device, initially, an MIP-axis is set. An operator sets a predetermined axis in a subject as an MIP-axis by operating the input unit 33. The MIP-axis denotes an axis orthogonal to each of directions for projecting an MIP image with respect to three-dimensional volume data. In Embodiment 1, a median line of a subject is set as an MIP-axis. Since the information acquired from an MIP image of a region of interest can be analyzed by correlating with an image suitable for a diagnosis of a whole-body image of a subject, it is more preferable to set a median line as an MIP-axis. The set MIP-axis information is transmitted to the position information calculation unit 21.

Step S2 (Generation of First Three-dimensional Volume Data)

Next, as first three-dimensional volume data, three-dimensional volume data for a left chest breast is generated. That is, radioactive pharmaceuticals labeled by positron-emitting radionuclide are administered to a subject. When a predetermined time has elapsed after the administration, as shown in FIG. 1B, a breast B of the left chest of the subject is inserted into the introduction hole 3. An operator operates the input unit 33 to input an instruction to detect an annihilation γ ray pair and information including a content that a region of interest is a breast of a left chest. Each of radiation detectors 7 transmits a γ ray detection signal from the light detector 13 to the concurrent counting unit 17 in accordance with the input instruction. For each of γ ray detection signals, information on the time when the γ ray is detected is given by a clock not illustrated.

The concurrent counting unit 17 analyzes each γ ray detection signal based on the time information given to the γ ray detection signal. When it is judged to be a γ ray detection signal based on an annihilation γ ray pair, the concurrent counting unit 17 judges that the γ ray detection signal is suitable data. The concurrent counting unit 17 judges that the pair of γ rays concurrently incident to a pair of scintillator blocks 9 facing each other across the center point Po is an annihilation γ ray pair caused by radiopharmaceuticals in the subject. The γ ray detection signal judged as proper data is transmitted from the concurrent counting unit 17 and γ ray signals other than the above will be discarded as noises.

The reconfiguration unit 19 reconfigures three-dimensional volume data related to the inner position of the breast B and the generation position of the annihilation γ ray pair based on the γ ray detection signal transmitted as proper data. Since the generation position of the annihilation γ ray pair denotes a distribution position of the radiopharmaceuticals, the three-dimensional volume data to be reconfigured denotes image data showing the distribution position of the radiopharmaceuticals in the breast B. The three-dimensional data of the breast of the left chest to be reconfigured will be referred to as "three-dimensional data LB". The three-dimensional data LB are transmitted to the position information calculation unit 21 and the tomographic image generation unit 31.

The position information calculation unit 21 calculates the coordinate position of the three-dimensional data LB with reference to the position of the MIP-axis. In a medical image, based on a standard, such as, e.g., DICOM (Digital Imaging and Communications in Medicine), a coordinate position in a subject of image data and a size of an imaging range of the image data are calculated using a specific position of the image data as a reference point. In the case of acquiring three-dimensional volume data like in Embodiment 1, the front side of the upper left end of the three-dimensional volume data is set as a reference point.

Figure 4:
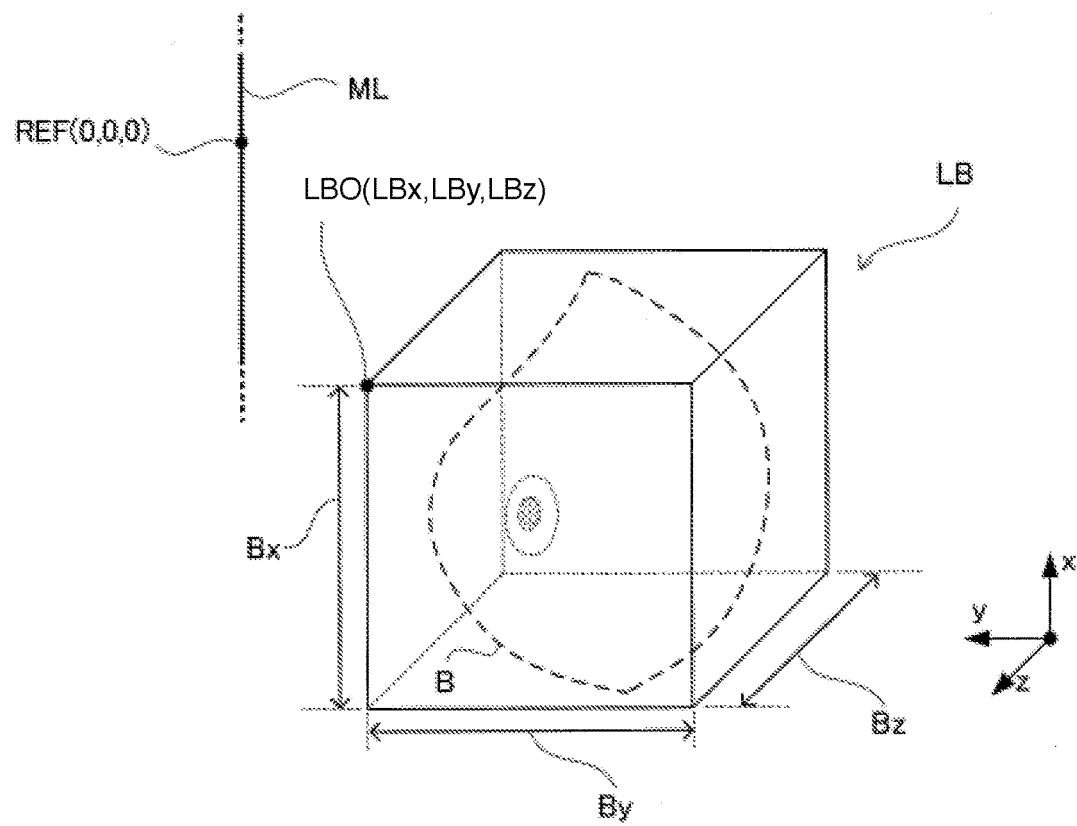
FIG. 4 is a schematic view showing a coordinate and a range of three-dimensional data generated in Embodiment 1.

Generally, a relative position of a breast of a left chest relative to a whole-body of a human body is almost the same among patients. Therefore, for example, by obtaining information on a height of a subject, the position information calculation unit 21 can set a predetermined region on a median line ML, which is an MIP-axis, as a standard position and calculate the information of the distance from the standard position (In Embodiment 1, "top of head") to the reference point of the three-dimensional data LB. As shown in FIG. 4, when the coordinate of the reference position REF which is a top of a head is defined as (0, 0, 0), the coordinate calculated for the reference point LBO of the three-dimensional data LB is defined as (LBx, LBy, LBz). Since the photographing range is determined according to the standard of the PET device, the length Bx in the x-direction, the length By in the y-direction, and the length Bz in the z-direction are calculated for the three-dimensional data LB.

Step S3 (Generation of Second Three-dimensional Volume Data)

After generating the three-dimensional data LB as first volume data, three-dimensional volume data for the breast of the right chest is generated as second volume data. The process in Step S3 is the same as Step S2. That is, the operator operates the input unit 33 with the breast B of the subject's right chest inserted in the introduction hole 3, and inputs an instruction to detect an annihilation γ ray pair and the information including contents that the region of interest is the breast of the right chest.

The concurrent counting unit 17 transmits the γ ray detection signal judged as proper data to the reconfiguration unit 19. The reconfiguration unit 19 reconfigures three-dimensional volume data in which the inside position of the breast B and the generation location of the annihilation γ ray pair are correlated. The three-dimensional volume data to be reconfigured for the breast of the right chest will be hereinafter referred to as "three-dimensional data RB". The three-dimensional data RB is transmitted to the position information calculation unit 21, and the position information calculation unit 21 calculates the coordinate position information of the three-dimensional data RB. It is defined that the coordinate calculated for the reference point RBO of the three-dimensional data RB is (RBx, RBy, RBz). The length of the three-dimensional data RB in each of the x-direction, the y-direction, and the z-direction is the same as that of the three-dimensional data LB.

Step S4 (Alignment of Three-dimensional Volume Data)

Figure 5:
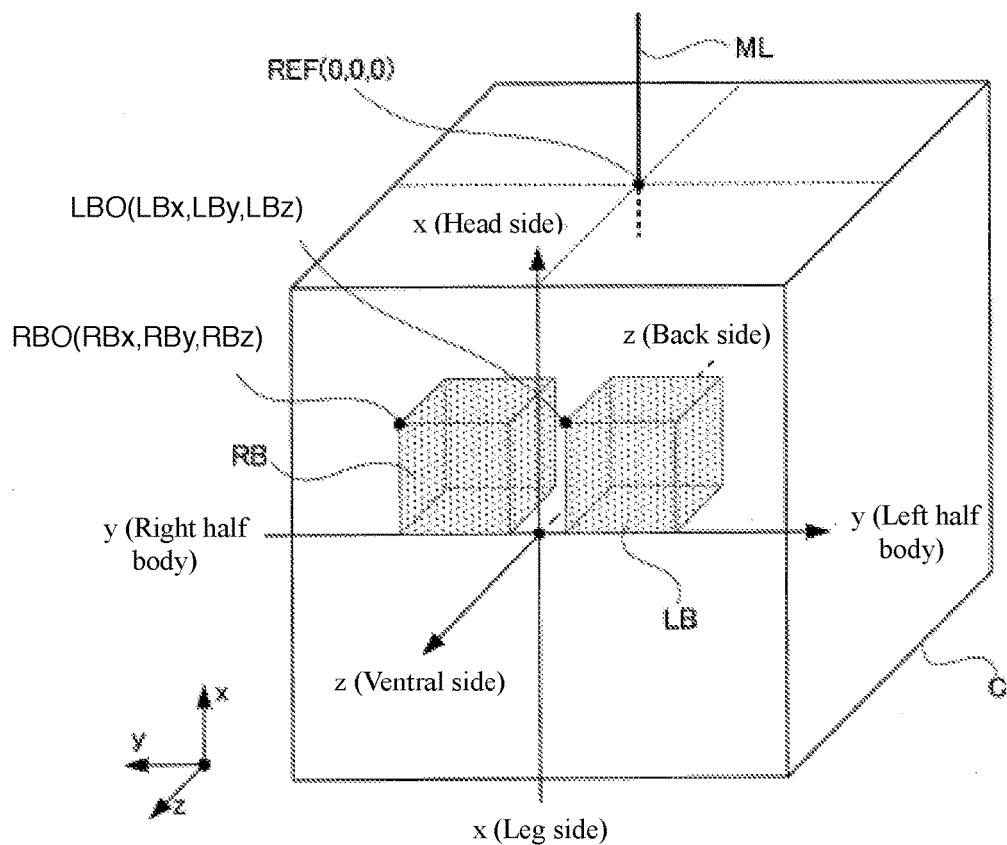
FIG. 5 is a schematic view showing a positional relationship between each of three-dimensional data and an upper body image in Step S3 according to Embodiment 1.

After the coordinate position is calculated for each of the three-dimensional data LB and RB, the position information calculation unit 21 performs alignment of each of the three-dimensional volume data. FIG. 5 schematically shows a relative position of the three-dimensional data LB and RB in a virtual whole-body image C. In FIG. 5, the direction advancing upward in the x-direction is defined as a direction of the head side of the subject, and the direction advancing forward in the z-direction is defined as a direction of the ventral side (front side) of the subject. A median line ML is a line that passes through the top of the head REF which is a standard position and is parallel to the body axis direction (x-direction) of the subject. Depending on the purpose of diagnoses, in place of the whole-body image C, an image with the MIP-axis as the center line of the axial surface, such as. e.g., an upper body image and a chest part whole image, may be used.

In the virtual whole-body image C, the position information calculation unit 21 determines the position of the three-dimensional data LB and the position of the three-dimensional data RB. Since the three-dimensional data LB is volume data obtained about the breast of the left chest of the subject, the data is located on the right front side as seen toward the front in the whole-body image C. The three-dimensional data LB is located on the left front side in the whole-body image C as seen toward the front.

The position information calculation unit 21 sets three-dimensional positions of the three-dimensional data LB and RB so as to match the positional relationship between the median line ML which is an MIP-axis and each of the regions of interest. Specifically, based on each of the coordinates of the reference position REF on the median line ML, the reference point LBO, and the reference point RBO, the position of the three-dimensional data LB and the position of the three-dimensional data RB in the whole-body image C are set. Each of the three-dimensional data in which alignment was performed is transmitted to the three-dimensional data integration unit 23.

Step S5 (Integration of Three-dimensional Volume Data)

After alignment of the three-dimensional volume data is performed, integration of the three-dimensional volume data is performed. That is, the three-dimensional data integration unit 23 integrates a plurality of three-dimensional volume data (three-dimensional data LB and RB) set at remote positions, and converts into single three-dimensional volume data. Single three-dimensional volume data generated by the integration will be referred to as three-dimensional data ALB. The three-dimensional data ALB generated by the three-dimensional data integration unit 23 corresponds to the integrated three-dimensional volume data of the present invention.

Figure 6:
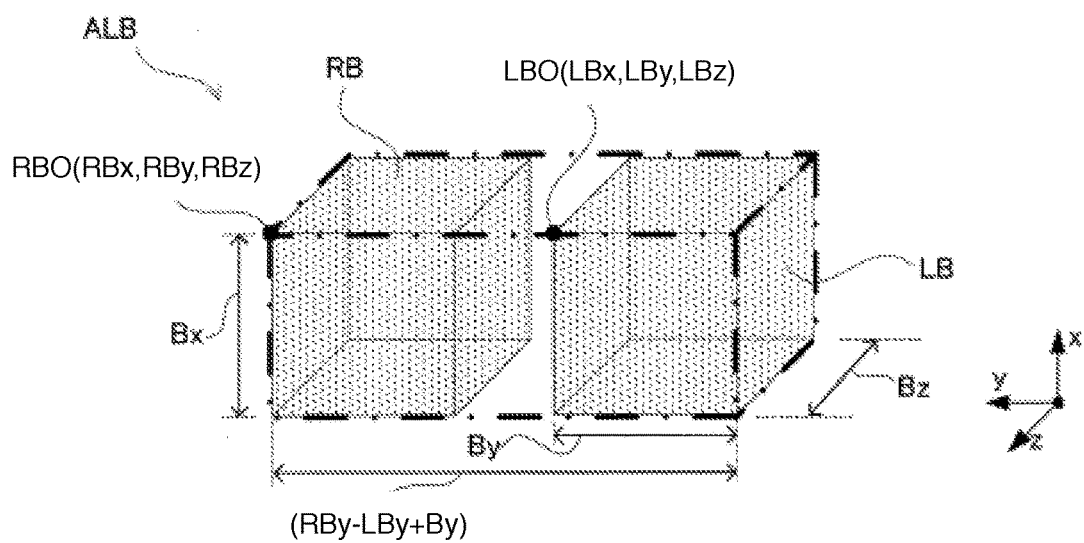
FIG. 6 is a schematic view showing a range for integrating the three-dimensional volume data in Step S4 according to Embodiment 1.

The range of the three-dimensional data ALB is a range covering all of the three-dimensional volume data to be integrated. Therefore, as shown in FIG. 6, the range of the three-dimensional data ALB is shown as a single rectangular parallelepiped surrounded by thick dot-and-dash lines encompassing all of the three-dimensional data LB and RB. In general, for each of the left and right breasts, the x-direction and z-direction co-ordinates are approximately the same. For the three-dimensional data ALB, the coordinate of the reference point is (RBx, RBy, RBz), the length in the x-direction is Bx, the length in the y-direction is (RBy−LBy+By), the length in the z-direction is Bz. The information of the three-dimensional data ALB is transmitted to the MIP image generation unit 27.

Step S6 (Generation of MIP Image)

Figure 7A:
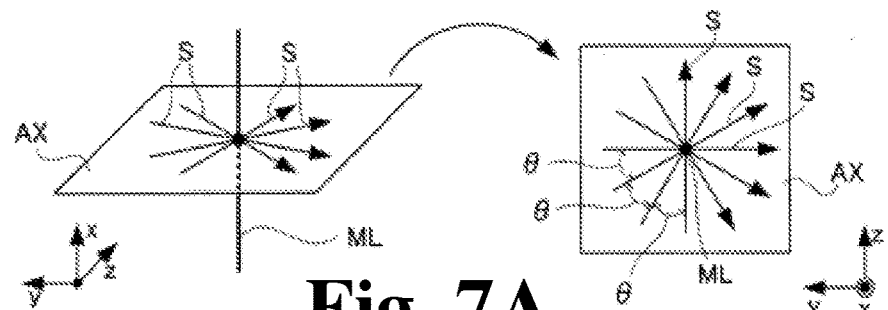
FIG. 7A is a view showing the positional relationship between each projection direction and an MIP-axis.

The MIP image generation unit 27 performs projection processing for the three-dimensional data ALB in a single or a plurality of projection directions S, respectively, and generates an MIP image A. As shown in FIG. 7A, each of the projection directions S is orthogonal to the median line ML which is an MIP-axis. The angle θ between projection directions positioned on the orthogonal plane AX (axial surface in Embodiment 1) of the MIP-axis and the number of MIP images to be generated (the number of projection directions) may be arbitrarily changed depending on the photographing conditions. For example, a total of 18 pieces of MIP images are generated over a range of 180° while changing the angle of the projection direction with respect to the median line ML by 10°. In this case, the angle of the projection direction S on the orthogonal plane AX is changed by 10°. The number of MIP images to be generated is more preferably about 10 to 20 pieces.

Figure 7B:
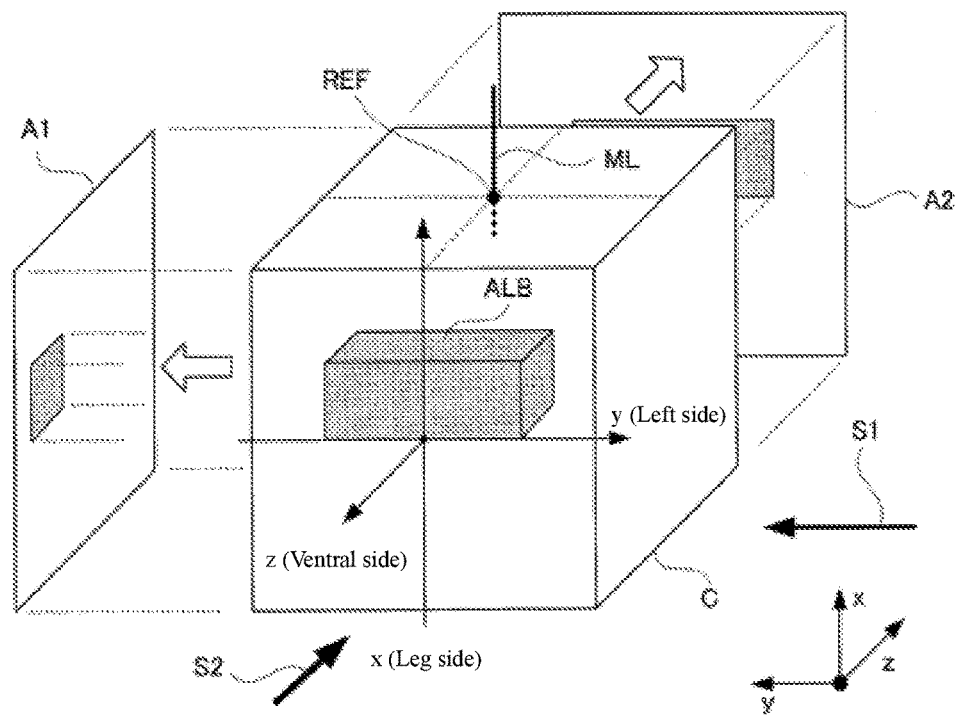
FIG. 7B is a view showing positional relationships of integrated three-dimensional volume data, MIP images projected, and each projection direction.
Figure 8:
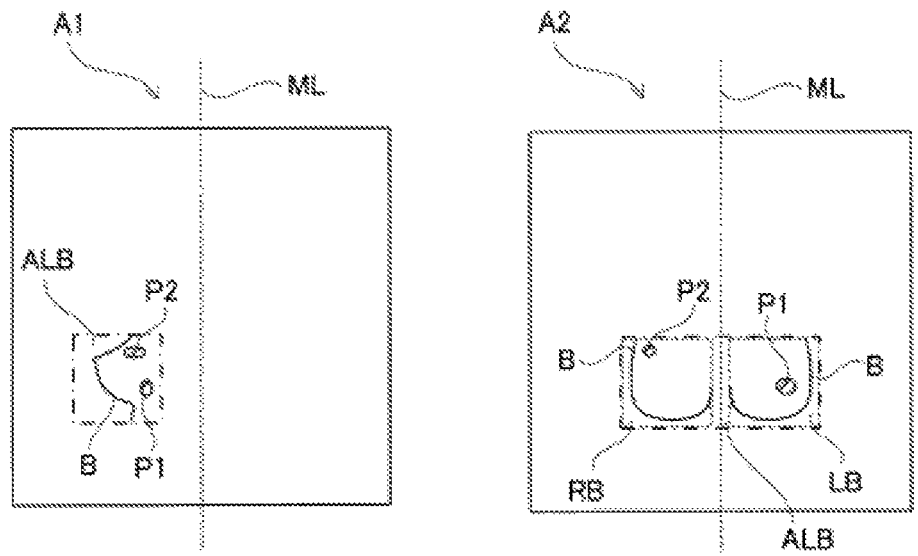
FIG. 8 is a view showing each of MIP images generated in Step S6 according to Embodiment 1.

In Embodiment 1, for the convenience of explanation, it is assumed that MIP images are generated in two directions by changing the angle of projection direction by 90°. That is, as shown in FIG. 7B, in two directions, i.e., the projection direction S1 orthogonal to the median line ML and parallel to the y-direction and the projection direction S2 orthogonal to the median line ML and parallel to the z-direction, MIP images are generated. The MIP image generation unit 27 generates the MIP image A1 in the projection direction S1 and generates the MIP image A2 in the projection direction S2 for the three-dimensional data ALB. The three-dimensional data ALB is shown in gray in FIG. 7.

In the MIP image A1, the projection image of the three-dimensional data LB and the projection image of the three-dimensional data RB are reflected in an overlapped manner. In the MIP image A2, the projection image of the three-dimensional data LB and the projection image of the three-dimensional data RB are reflected side by side. In each of the MIP images A, a radiopharmaceutical accumulation point P1 in the breast of the left chest and a radiopharmaceutical accumulation point P2 in the breast of the right chest appear. Each of the generated MIP images is transmitted to the superimposed image generation unit 29.

Step S7 (Generation of Superimposed Image)

Figure 9:
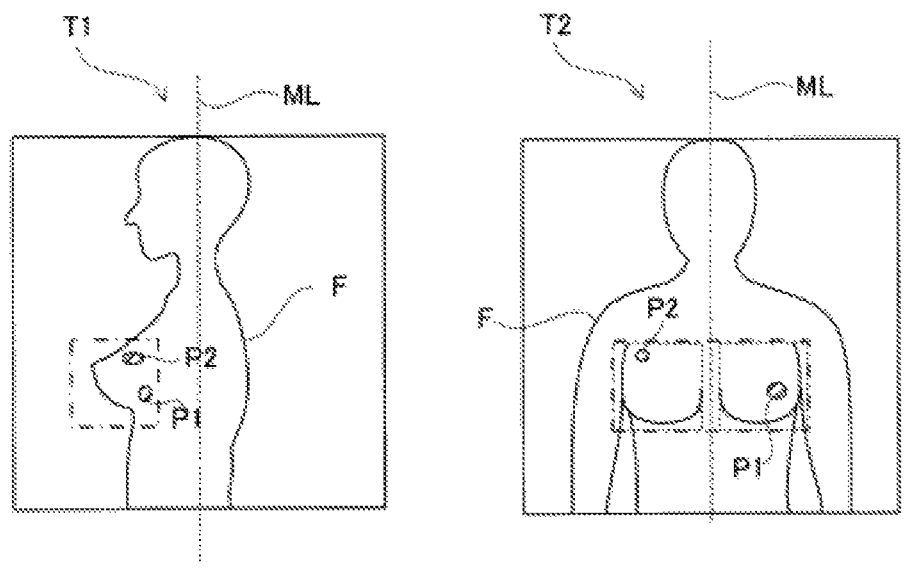
FIG. 9 is a view showing each of superimposed images generated in Step S7 according to Embodiment 1.

The superimposed image generation unit 29 generates a superimposed image T by performing image processing for superimposing a comparison image on each of the MIP images. As the comparison image, an image such as a whole-body image or a whole upper body image of a subject (or a standard-sized human body) in which an MIP-axis is set to a center line of an axial surface is used. In Embodiment 1, as shown in FIG. 9, an upper body image of a subject is used as a comparison image F. As shown in FIG. 9, a superimposed image T generated based on the MIP image A1 will be denoted as a superimposed image T1. A superimposed image T generated based on the MIP image A2 will be denoted as a superimposed image T2. Each of the generated superimposed images T is displayed on the monitor 37.

The comparison image F to be superimposed on each of the MIP images A is an image obtained by projecting the three-dimensional volume data of the upper body of the subject in the same projection direction as each of the MIP images A. Specifically, the comparison image F to be superimposed on the MIP image A1 is an image obtained by projecting the upper body of the subject in the projection direction S1 (y-direction). On the MIP image A2, an image obtained by projecting the upper body of the subject in the projection direction S2 (z-direction) is superimposed as a comparison image F. Both the MIP image A and the comparison image F are images projected in the projection direction with the median line as an MIP-axis. Therefore, by referring to the comparison image F displayed on the superimposed image and the accumulation point of radiopharmaceuticals, the operator can diagnose the position of the radiopharmaceutical accumulation point appearing on the MIP image more preferably in association with the entire upper body of the subject.

Step S8 (Display of Tomographic Image)

Figure 10A:
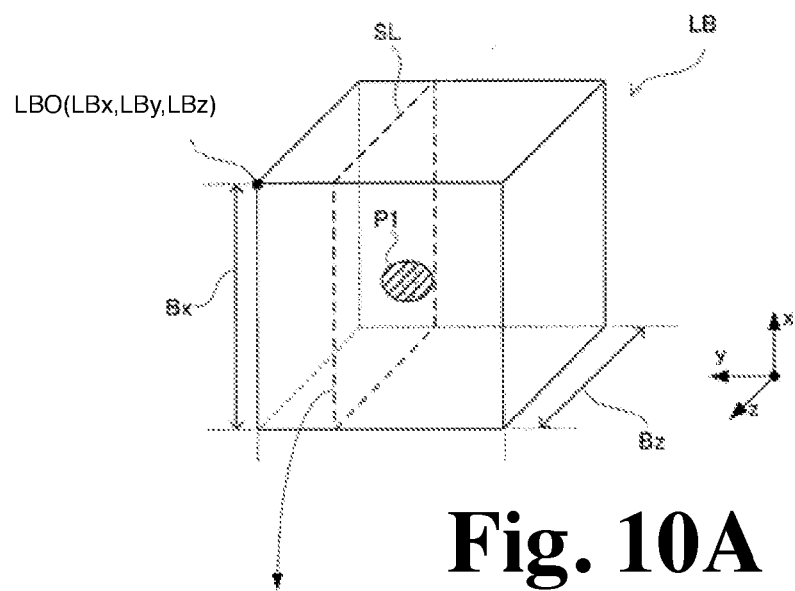
FIG. 10A is a view showing a slice surface with respect to three-dimensional volume data.
Figure 10B:
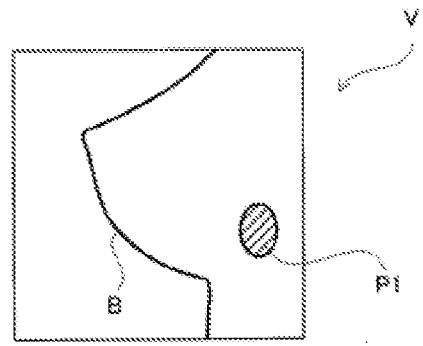
FIG. 10B is a view showing a tomographic image at the slice surface.

An operator refers to the superimposed image displayed on the monitor 37, and confirms approximate positional information on the radiopharmaceutical accumulation point P in the breast of the subject. Then, the operator operates the input unit 33 based on the confirmed positional information, and sets a position of a slice surface SL for generating a tomographic image from the three-dimensional volume data. As shown in FIG. 10, the tomographic image generation unit 31 generates a tomographic image V on the slice surface SL set for the three-dimensional data LB. The generated tomographic image V is displayed on the monitor 37 by the tomographic image generation unit 31. Using the tomographic image V, the operator performs more precise diagnoses about the radiopharmaceutical accumulation point P1 in the breast B of the left chest.

<Effects by Configuration of Embodiment 1>

As described above, by using the PET device 1 equipped with the tomographic image display device 15 according to Embodiment 1, it is possible to more preferably diagnose a plurality of regions of interest in association with the information of the whole body image of the subject. Hereinafter, effects by the configuration of Embodiment 1 will be described.

Figure 11A:
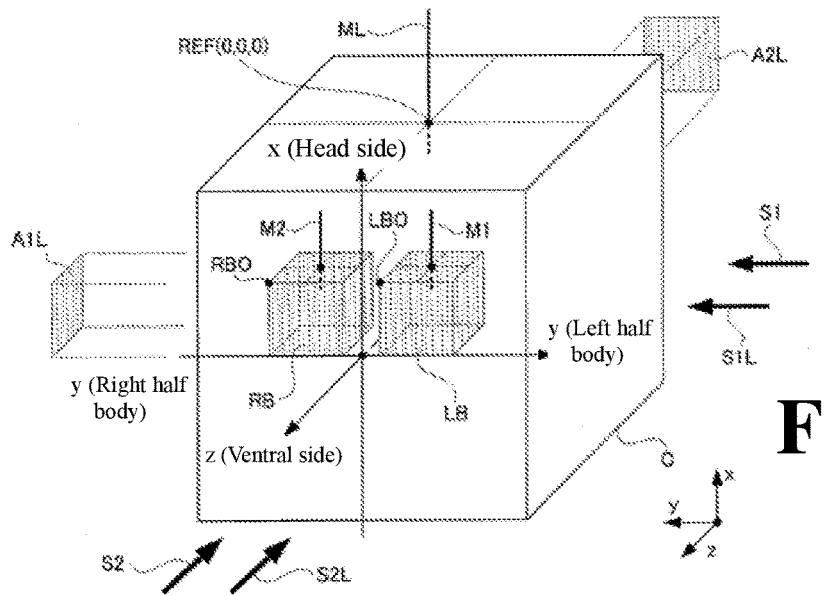
FIG. 11A is a view showing a relationship between three-dimensional volume data and projection directions of MIP images in a conventional embodiment.

In a conventional tomographic image display device using a sliding method, when three-dimensional volume data is generated for a region of interest outside the median line, the position of the MIP-axis is shifted to the center line of the region of interest according to the movement of the region of interest. Then, in a single or a plurality of projection directions with the MIP-axis after the movement as a rotation axis, a series of MIP images are generated for the region of interest. That is, when the region of interest is a breast of a left chest, in a conventional device, as shown in FIG. 11A, the position of the MIP-axis moves from the median line ML to the center line M1. The center line M1 is a line that passes through the center point of the three-dimensional data LB obtained for the breast of the left chest and is parallel to the z-direction. Also, when the region of interest is the breast of the right chest, the center line M2 that passes through the center point of the three-dimensional data RB and is parallel to the z-direction is an MIP-axis. That is, in a conventional apparatus, the position of the MIP-axis is also changed according to the change of the region of interest.

Figure 11B:
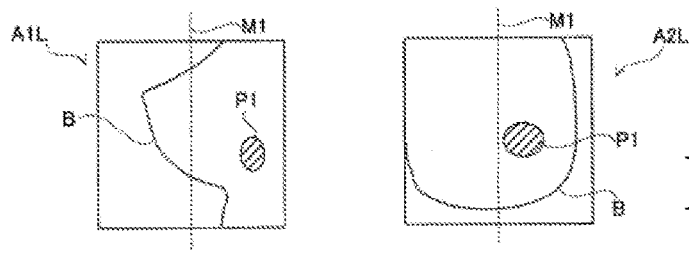
FIG. 11B is a schematic view showing an image reflected in an MIP image generated in a conventional embodiment.

In a conventional apparatus, when a region of interest is a breast of a left chest, each of the directions for projecting the MIP image of the three-dimensional data LB is orthogonal to the center line M1 which is an MIP-axis. Accordingly, for example, MIP images of the three-dimensional data LB are generated in the projection direction S1L parallel to the y-direction and orthogonal to the center line M1, the projection direction S2L parallel to the z-direction and orthogonal to the center line M1, and the like. The radiopharmaceutical accumulation point P1 in the breast B of the left chest appears in the MIP image A1L of the three-dimensional data LB projected in the projection direction S1L and the MIP image A2L of the three-dimensional data LB projected in the projection direction S2L (FIG. 11B).

The MIP images A1L and A2L are images reflecting the breast B of the left chest with the center line M1 of the three-dimensional data LB as a center line of the image. When a series of MIP images including the MIP images A1L and A2L are successively displayed, a moving image for rotating the image of the breast B of the left chest about the center line M1 as a rotational axis which is an MIP-axis is generated. Such a series of MIP images are useful when performing diagnoses only focusing on the breast of the left chest.

On the other hand, in the MIP image reflecting only the breast B of the left chest, diagnoses cannot be performed by associating the radiopharmaceutical accumulation point P1 in the breast of the left chest with the whole-body image (or the whole chest image) of the subject. That is, in a conventional apparatus, it is difficult to analyze the information obtained for a specific region of interest by the MIP image in association with the image information of the whole body. As a result, since the information obtained by analyzing the MIP image is limited, there is a concern that the range of diagnoses that can be performed using the MIP image is limited.

Figure 11C:
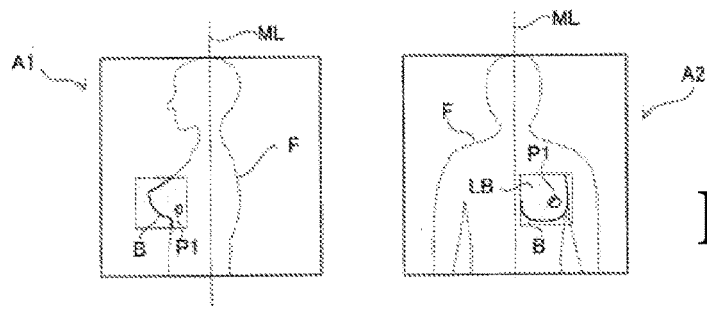
FIG. 11C is a schematic view showing an image reflected in an MIP image generated in Embodiment 1.

Therefore, in the tomographic image display device according to Embodiment 1, the MIP-axis setting unit 20 is configured to set a median line ML of a subject as an MIP-axis regardless of the position of the region of interest. That is, even in cases where the region of interest is a breast of a left chest, the MIP image generation unit 27 generates an MIP image with the median line ML as an MIP-axis. Accordingly, MIP images of the three-dimensional data LB are generated in the projection direction S1 parallel to the y-direction and orthogonal to the center line ML, the projection direction S2 parallel to the z-direction and orthogonal to the center line ML, and the like. The MIP image A1 projected in the projection direction S1 and the MIP image A2 projected in the projection direction S2L are images reflecting the breast B of the left chest in which the median line ML is the center line of the image (FIG. 11C).

In each of a series of MIP images including the MIP images A1 and A2, the projection image of the three-dimensional data LB is reflected at a position corresponding to the breast B of the left chest with respect to the median line of the subject. That is, even in the case of generating MIP images for the region of interest outside the median line like the breast of the left chest, in the same manner as in the case of generating MIP images with the whole-body as a region of interest, images clear in the positional relationship between the breast and the median line can be generated.

Therefore, an operator can easily and accurately confirm the positional relationship between the radiopharmaceutical accumulation point P1 in the breast B of the left chest and the whole-body of the subject using a series of MIP images with the median line ML as an MIP-axis. Therefore, it is possible to perform more various diagnoses using MIP images. Furthermore, by superimposing a comparison image F, such as, e.g., a whole-body image or an upper body image of a subject, on MIP images with reference to the median line ML which is an MIP-axis, the positional relationship between the radiopharmaceutical accumulation point P1 and the whole-body of the subject can be confirmed more accurately.

By always setting an MIP-axis to a median line of a subject, regardless of a position of a region of interest, it is possible to perform diagnoses by associating the information obtained from the MIP images of the region of interest with the whole-body image of the subject. In addition, the superimposed image generation unit 29 superimposes a whole body image of a subject, etc. as a comparison image on each of MIP images, to generate a superimposed image. By referring to the MIP image projected from the three-dimensional data and the comparison image superimposed on the MIP image, the operator can perform more accurate overview diagnoses in which the information obtained from the MIP images of the region of interest and the whole-body image of the subject are associated.

The tomographic image display device according to Embodiment 1 is provided with a three-dimensional data integration unit 23. The three-dimensional data integration unit 23 integrates each of the three-dimensional volume data obtained for two or more separated regions of interest into single three-dimensional volume data. That is, in cases where a breast of a left chest and a breast of a right chest are set as regions of interest, the three-dimensional data integration unit 23 integrates three-dimensional data LB and RB to generate single three-dimensional data ALB.

The MIP image generation unit 27 generates an MIP image of the integrated three-dimensional data ALB with the median line ML as an MIP-axis. In this case, the projection image of the three-dimensional data is reflected in the MIP image for each of the breast of the left chest and the breast of the right chest. That is, the projection images of a plurality of regions of interest are reflected on the single MIP image at positions associated with the whole-body of the subject. In this case, overview diagnoses can be performed on a plurality of regions of interest based on a single MIP image. Therefore, by using the device according to Embodiment 1, it is possible to reduce the burden on the operator when a plurality of regions are diagnosed for one patient.

Embodiment 2

Figure 12:
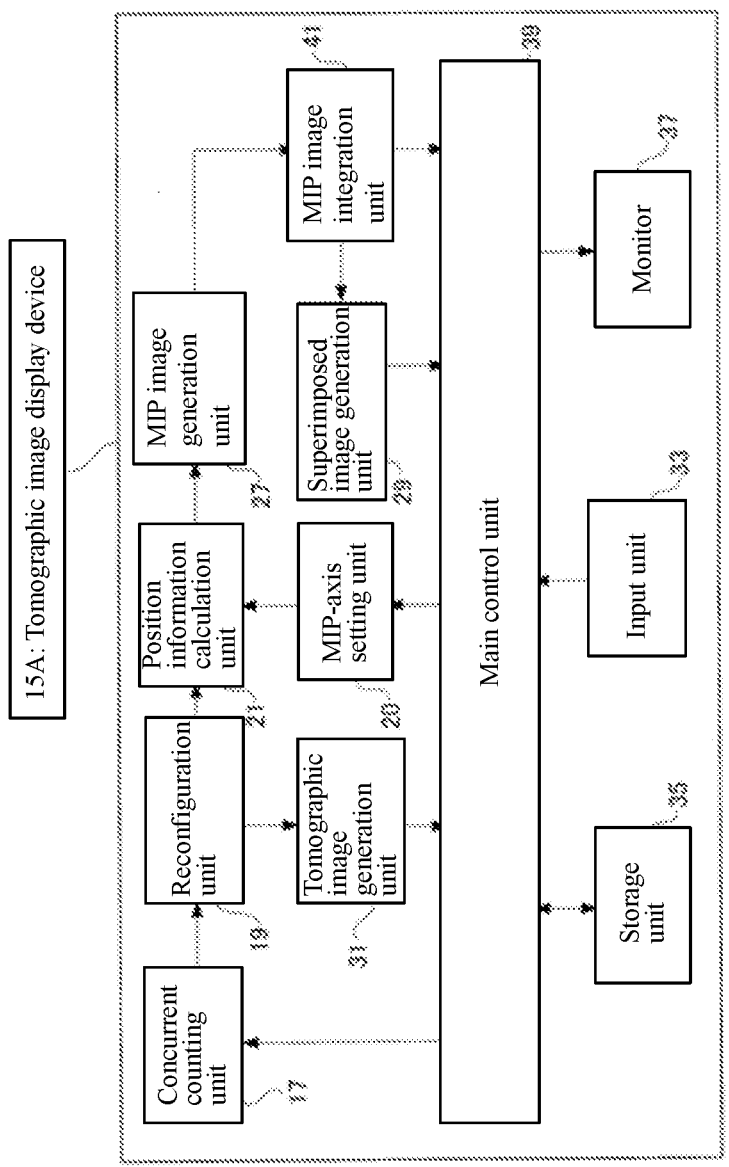
FIG. 12 is a functional block diagram explaining a structure of a PET device equipped with a tomographic image display device according to Embodiment 2.

Hereinafter, Embodiment 2 of the present invention will be described with reference to drawings. The overall configuration of the tomographic image display device 15A according to Embodiment 2 is the same as that of the tomographic image display device 15 according to Embodiment 1. However, the tomographic image display device 15 according to Embodiment 1 is provided with a three-dimensional data integration unit 23, but the tomographic image display device 15A according to Embodiment 2 is provided with an MIP image integration unit 41 in place of the three-dimensional data integration unit 23 as shown in FIG. 12. The MIP image integration unit 41 is provided at the post-stage of the MIP image generation unit 27. The MIP image integration unit 41 integrates MIP images acquired in the same projection direction among a series of MIP images acquired for different regions of interest, and reconfigures them as a single MIP image.

Figure 3A:
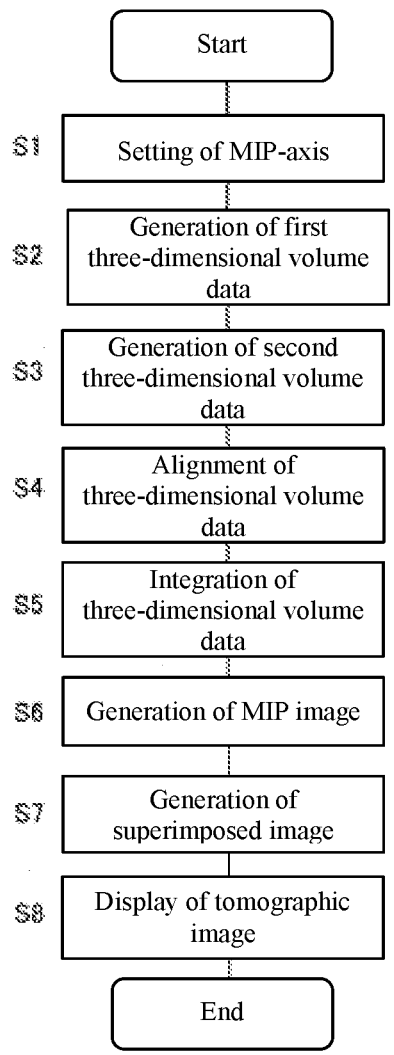
FIG. 3A is a flowchart of Embodiment 1.

That is, in Embodiment 1, as shown in FIG. 3A, after alignment is performed for each of three-dimensional volume data obtained for a plurality of regions of interest (Step S4), each of three-dimensional volume data is integrated (Step S5). Then, for the integrated data, a series of MIP images are generated with the median line as an MIP-axis (Step S6).

Figure 3B:
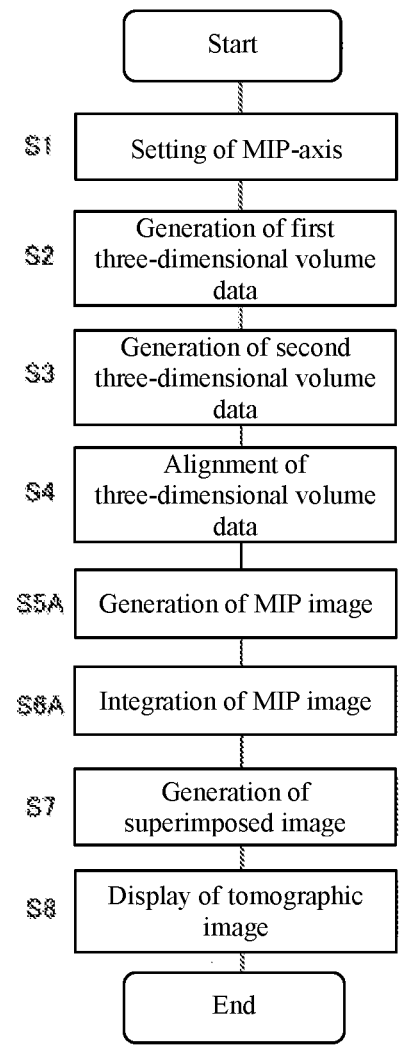
FIG. 3B is a flowchart of Embodiment 2.

On the other hand, in Embodiment 2, as shown in FIG. 3B, after alignment is performed for each of three-dimensional volume data obtained for a plurality of regions of interest (Step S4), a series of MIP images are generated with the median line as an MIP-axis for each of three-dimensional volume data (Step S5A). Thereafter, MIP images generated in the same projection direction are superimposed with each other with reference to the MIP-axis to generate a single MIP image (hereinafter referred to as "integrated image") in which the projection images of a plurality of regions of interest are reflected (Step S6A).

Here, the operation of the tomographic image display device 15A according to Embodiment 2 will be described with emphasis on the process of Steps S5A to S6A characteristic to Embodiment 2. In the same manner as in Embodiment 1, a case in which a breast of a left chest and a breast of a right chest are set as a region of interest, respectively, and the projection directions are S1 and S2 will be described. Since the processes of Steps S1 to S4 are the same as those of Embodiment 1, the description will be omitted.

Step S5A (Generation of MIP Image)

As shown in FIG. 5, after the position information calculation unit 21 performed alignment of the three-dimensional data LB and RB, the MIP image generation unit 27 generates MIP images. That is, the MIP image generation unit 27 generates the MIP image AL of the three-dimensional data LB with the median line ML as an MIP-axis and the MIP image AR of the three-dimensional data RB with the median line ML as an MIP-axis.

Figure 13:
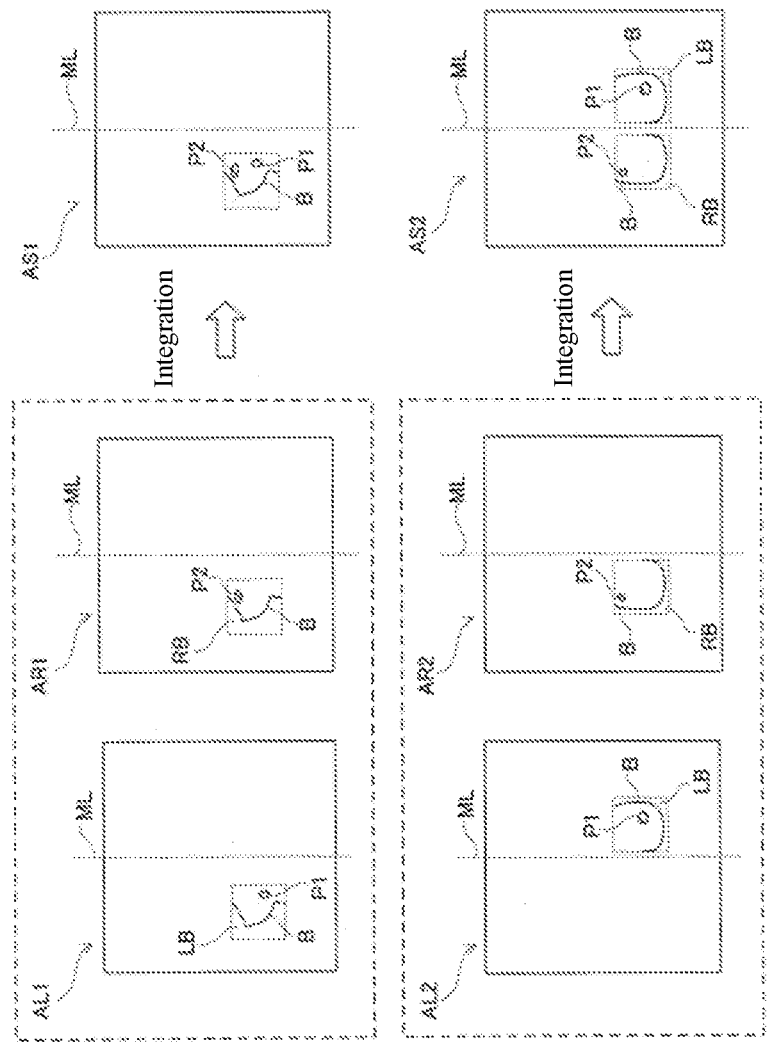
FIG. 13 is a view showing MIP images to be integrated in Step S6A according to Embodiment 2.
Figure 14B:
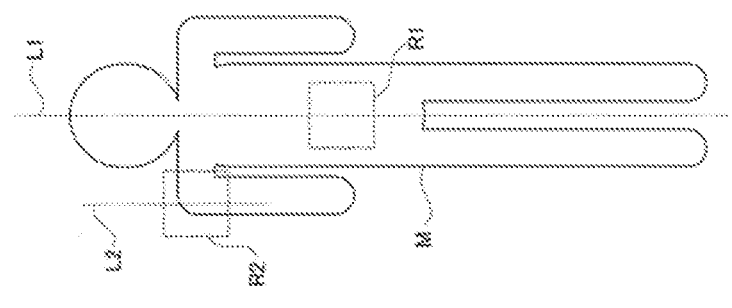
FIG. 14B is a view showing a positional relationship between regions of interest and an MIP-axis.
Figure 14A:
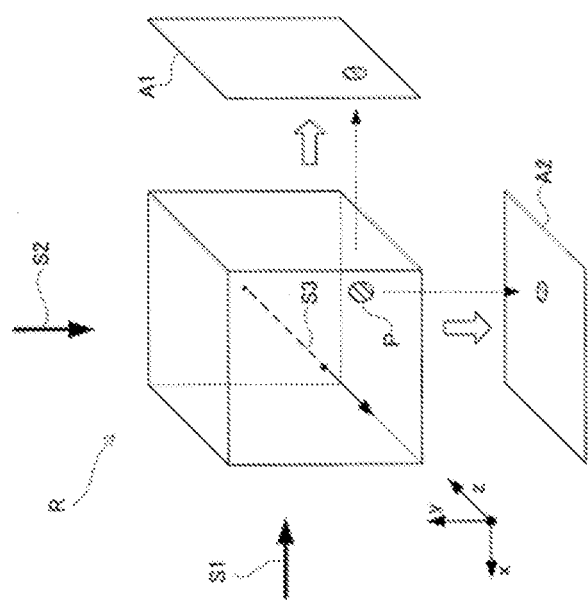
FIG. 14A is a schematic view showing a positional relationship between three-dimensional data and MIP images in a conventional embodiment.

Among MIP images AL, the image projected in the projection direction S1 is denoted as an MIP image AL1 and the image projected in the projection direction S2 is denoted as an MIP image AL2 (FIG. 13, middle column). Further, among the MIP images AR, the image projected in the projection direction S1 is denoted as an MIP image AR1 and the image projected in the projection direction S2 is denoted as an MIP image AR2 (FIG. 13, middle column). In each of the MIP images AL, the projection image of the three-dimensional data AL appears at the position corresponding to the breast of the left chest in the whole-body of the subject. In each of the MIP images AR, the projection image of the three-dimensional data AL appears at the position corresponding to the breast of the right chest in the whole-body of the subject. Each of the MIP images is transmitted to the MIP image integration unit 41.

Step S6A (Integration of MIP Image)

The MIP image integration unit 41 integrates MIP images projected in the same projection direction and generates an integrated image AS. That is, the MIP image AL1 and the MIP image AR1, which are MIP images projected in the projection direction S1, are integrated to generate an integrated image AS1. Then, the MIP image AL2 and the MIP image AR2, which are MIP images projected in the projection direction S2, are integrated to generate an integrated image AS2 (FIG. 13, right column). In each of the integrated images AS, the left and right breast B appear at positions corresponding to the whole-body of the subject, respectively. The integrated image AS corresponds to the integrated MIP image in the present invention.

The integrated images AS are transmitted to the superimposed image generation unit 29, and the superimposed image generation unit 29 superimposes the comparison image F on the integrated images AS to generate a superimposed image (Step S7). An operator determines a position of an appropriate slice surface by referring to the integrated images AS, and makes the monitor 37 display the tomographic image at the determined slice surface (Step S8). The operator performs diagnoses of the regions of interest based on the tomographic images.

In this way, in Embodiment 2, by integrating MIP images, a single MIP image is generated for each projection direction, in which a plurality of regions of interest are respectively displayed at positions corresponding to the whole-body of the subject. In this case, the target to be integrated by the MIP image integration unit 41 is not the entire three-dimensional volume data but each MIP image. Therefore, it is possible to simplify the calculation required to generate MIP images in which each of regions of interest appears at a position corresponding to the whole-body of the subject, respectively. Therefore, by using the device according to Embodiment 2, it is possible to further improve the diagnosis workflow.

The present invention is not limited to the above Embodiments, and can be modified as follows.

(1) In each of the aforementioned Embodiments, in Step S2 and Step S3, for two regions of interest, three-dimensional volume data were reconfigured, respectively. However, the number of regions of interest may be increased or decreased as appropriate. In this case, the number of Steps to reconfigure three-dimensional volume data according to the number of regions of interest will increase or decrease. Also, in cases where the number of regions of interest is one, the process of integrating three-dimensional volume data (MIP images in FIG. 2) is omitted.

(2) In each of the aforementioned Embodiments, the position of the MIP-axis is always set to the median line, but not limited thereto. That is, when the MIP-axis of each region of interest matches, the position of the MIP-axis set by the MIP-axis setting unit 20 may be other than a median line. For example, when a thumb and a little finger are set as regions of interest, MIP images are generated with a line connecting the middle finger and the wrist set as an MIP-axis. Then, by superimposing an image of a whole hand as a comparison image on the MIP image, the information obtained for each of the thumb and the little finger can be analyzed in association with the position of the whole hand.

(3) In each of the aforementioned Embodiments, the description was made by exemplifying the case in which diagnoses were made with respect to a subject in a standing posture or a sitting posture. However, the configuration according to the present invention can also be applied to the case in which diagnoses are made with respect to a subject arranged in a supine position on a tabletop.

(4) In each of the aforementioned Embodiments, a PET device has been described as an example in which a tomographic image display device is provided. However, a tomographic image display device according to each Embodiment may also be used, in addition to a PET device, a tomographic image diagnosis apparatus such as a SPECT apparatus.

DESCRIPTION OF SYMBOLS

1 PET device
7 radiation detector
13 light detector
15 tomographic image display device
17 concurrent counting unit
19 reconfiguration unit (three-dimensional data generation means)
20 MIP-axis setting unit (central axis setting means)
21 position information calculation unit (alignment means)
23 three-dimensional data integration unit (three-dimensional data integration means)
27 MIP image generation unit (MIP image generation means)
29 superimposed image generation unit (superimposed image generation means)
31 tomographic image generation unit (tomographic image generation means)
33 input unit
35 storage unit
37 monitor (image display means)
39 main control unit
41 MIP image integration unit (MIP image integration means)

The invention claimed is:
1. A tomographic image display device comprising:
three-dimensional data generation means for generating three-dimensional volume data showing a generation position of radiation in a region of interest of a subject based on the radiation generated from the region of interest;
central axis setting means for setting a predetermined axis in the subject as a central axis;
alignment means for setting a three-dimensional position of the three-dimensional volume data to a three-dimensional position of the region of interest with respect to the central axis;
MIP image generation means for generating an MIP image which is a maximum intensity projection image by projecting a maximum pixel value in one or more projection directions orthogonal to the central axis with respect to the three-dimensional volume data in which the three-dimensional position is set by the alignment means;

tomographic image generation means for generating a tomographic image at a predetermined slice surface of the three-dimensional volume data; and image display means for displaying the MIP image and the tomographic image.

2. The tomographic image display device as recited in claim 1, further comprising three-dimensional data integration means for integrating a plurality of the three-dimensional volume data in which the three-dimensional position is set by the alignment means and converting them into single integrated three-dimensional volume data, wherein the MIP image generation means generates the MIP image in one or more projection directions orthogonal to the central axis with respect to the integrated three-dimensional volume data converted by the three-dimensional data integration means.

3. The tomographic image display device as recited in claim 1, further comprising MIP image integration means for generating an integrated MIP image by superimposing the MIP images projected in the same projection direction among the MIP images generated for a plurality of regions of interest with reference to a position of the central axis, wherein the image display means displays the integrated MIP image.

4. The tomographic image display device as recited in claim 1, further comprising superimposed image generation means for generating a superimposed image by superimposing an image in which all or a part of the subject is projected in the same projection direction as the MIP image on each of the MIP images generated by the MIP image generation means with reference to the position of the central axis, wherein the image display means displays the superimposed image.

5. The tomographic image display device as recited in claim 1, wherein the central axis is a median line of the subject.

* * * * *